(12) United States Patent
Nakai (10) Patent No.: US 9,907,864 B1
(45) Date of Patent: Mar. 6, 2018

(54) METHOD FOR SPECIFYING LEAKAGE PART OF CEREBROSPINAL FLUID IN CEREBROSPINAL FLUID HYPOVOLEMIA PATIENT, AND METHOD FOR TREATING CEREBROSPINAL FLUID HYPOVOLEMIA

(71) Applicant: NATIONAL UNIVERSITY CORPORATION KOCHI UNIVERSITY, Kochi (JP)

(72) Inventor: Eiichi Nakai, Kochi (JP)

(73) Assignee: NATIONAL UNIVERSITY CORPORATION KOCHI UNIVERSITY, Kochi (JP)

( * ) Notice: Subject to any disclaimer, the term of this patent is extended or adjusted under 35 U.S.C. 154(b) by 0 days.

(21) Appl. No.: 15/241,445

(22) Filed: Aug. 19, 2016

(51) Int. Cl.
A61B 5/055 (2006.01)
A61K 49/00 (2006.01)
A61K 35/14 (2015.01)

(52) U.S. Cl.
CPC .......... *A61K 49/0004* (2013.01); *A61K 35/14* (2013.01)

(58) Field of Classification Search
CPC .......... A61K 49/0004; A61B 5/150961; A61B 2010/0077; A61B 5/055; A61B 5/4824; A61B 5/743
USPC .......................................... 600/594; 424/9.3
See application file for complete search history.

(56) References Cited

PUBLICATIONS

Luetmer et al., Dynamic CT Myelography: A Technique for Localizing High-Flow Spinal Cerebrospinal Fluid Leaks, AJNR: Sep. 24, 2003, p. 1711-1714.*
Chazen et al., MR Myelography for Identification of Spinal CSF Leak in Spontaneous Intracranial Hypotension, American Journal of Neuroradiology Oct. 2014, 35 (10) 2007-2012.*
Franzini et al., "Intracranial spontaneous hypotension associated with CSF cervical leakage successfully treated by lumbar epidural blood patch", Acta Neurochir, vol. 152, 2010, pp. 1997-1999.
Rai et al., "Epidural Blood Patch at C2: Diagnosis and Treatment of Spontaneous Intracranial Hypotension", AJNR Am J Neuroradiol, vol. 26, Nov./Dec. 2005, pp. 2663-2666.
Mehta et al., "Repeated large-volume epidural blood patches for the treatment of spontaneous intracranial hypotension", Can J Anesth/J Can Anesth, vol. 56, 2009, pp. 609-613.
Watanabe et al., "Fluoroscopically guided epidural blood patch with subsequent spinal CT scans in the treatment of spontaneous cerebrospinal fluid hypovolemia", J Neurosurg, vol. 114, 2011, pp. 1731-1735.
Thomas et al., "Radionuclide Cisternography in Detecting Cerebrospinal Fluid Leak in Spontaneous Intracranial Hypotension", Clinical Nuclear Medicine, vol. 34, No. 7, Jul. 2009, pp. 410-416.
Nakai et al., "Use of fat-suppressed T2-weighted sagittal images after infusion of excess saline into the subarachnoid space as a new diagnostic modality for cerebrospinal fluid hypovolemia: technical note", J Neurosurg, vol. 124, 2016, pp. 580-583, 2016.
The 74th Annual Meeting of the Japan Neurosurgical Society, Oct. 2016, with partial English translation.
The 15th Annual Meeting of Japan CSF Hypovolemia Society, Term Saturday, Mar. 12 and Sunday, Mar. 13, 2016, with partial English translation.
The 12th citizen open lecture of the Japan Neurosurgical Society Chugoku Shikoku Branch, Sunday, Apr. 3, 2016, with partial English translation.
A program and proceedings of the 39th Annual Meeting of Japan Society of Neurotraumatology, Friday, Feb. 26 and Saturday 27, 2016.

* cited by examiner

*Primary Examiner* — Michael G Hartley
*Assistant Examiner* — Nabila G Ebrahim
(74) *Attorney, Agent, or Firm* — Wenderoth, Lind & Ponack, L.L.P.

(57) ABSTRACT

The objective of the present invention to provide a method for accurately and safely specifying a leakage part of cerebrospinal fluid in a cerebrospinal fluid hypovolemia patient, and a method for effectively treating cerebrospinal fluid hypovolemia with utilizing the specifying method. The method for specifying a leakage part of cerebrospinal fluid in a cerebrospinal fluid hypovolemia patient according to the present invention is characterized in comprising the steps of injecting saline into a bone-marrow space of a spine of the cerebrospinal fluid hypovolemia patient, and detecting the cerebrospinal fluid or the injected saline leaked from a dura mater of the spine to specify the leakage part of the cerebrospinal fluid.

8 Claims, 9 Drawing Sheets

METHOD FOR SPECIFYING LEAKAGE PART OF CEREBROSPINAL FLUID IN CEREBROSPINAL FLUID HYPOVOLEMIA PATIENT, AND METHOD FOR TREATING CEREBROSPINAL FLUID HYPOVOLEMIA

TECHNICAL FIELD

The present invention relates to a method for accurately specifying a leakage part of cerebrospinal fluid in a cerebrospinal fluid hypovolemia patient without difficulty, and a method for effectively treating cerebrospinal fluid hypovolemia.

BACKGROUND ART

Cerebrospinal fluid hypovolemia (CSFH) is caused by reducing an amount of cerebrospinal fluid (CSF) due to some causes. A CSFH patient presents with headache, neck pain, dizziness, tinnitus, fatigue or the like as a symptom. In general, CSFH is considered to be treatable; however, CSFH has a problem that it is difficult to diagnose CSFH. Specifically, it is exemplified as a main cause of CSFH that CSF, which fills cerebrospinal cavum around brain and spinal cord, persistently or intermittently leaks out due to high impact on body or head by traffic accident or the like. However the causal relationship between the cause and symptom is hardly specified, since it takes time to experience a symptom from the cause arises.

In order to treat CSFH, it is very important to specify a leakage part of CSF. Specifically, epidural blood patch is effective for treating CSFH caused by a leakage of CSF (Non-patent Documents 1 to 4). In epidural blood patch, autologous blood is injected into extradural space at a leakage part of CSF and coagulated to patch the leakage part. However, when a leakage part of CSF is not specified, epidural blood patch cannot be effectively carried out. It is therefore very important to specify the leakage part for the treatment of CSFH. However, it is very difficult to specify a leakage part of CSF, since a leakage of CSF is persistent and a leakage amount is very small.

When a patient is suspected to have CSFH, firstly, a spine image is generally taken by magnetic resonance imaging (MRI). MRI is safe, since it is not needed in MRI to use a medicine. It is however difficult by MRI to determine whether CSF leaks or not and to specify the leakage part. Then, CSF pressure is measured by lumbar puncture. If CSF pressure is lower than 6 cm $H_2O$, a patient is diagnosed with CSFH. However, a leakage part of CSF cannot be specified by measuring CSF pressure.

In order to specify a leakage part of CSF, computed tomography (CT) myelography and radio isotope (RI) cerebral scintigraphy are generally carried out (Non-patent Document 5). In CT myelography, a contrast medium is injected into bone-marrow space and a diffusion image of the injected contrast medium is taken using X-ray. In RI cerebral scintigraphy, RI is injected into bone-marrow space and an image of a spinae is taken using a gamma camera, by which radiation dose can be recognized. In addition, MRI myelography with using a contrast medium is carried out in some cases. However, as described above, it is very difficult to specify the leakage part, since a leakage amount of CSF is small. In particular, when the leakage part is in upper part of a spine, it is more difficult to specify the leakage part, since a contrast medium and RI are injected by lumbar puncture and the concentrations thereof become lower in upper part of a spine. It is therefore needed to take images multiple times in the diagnosis using the above-described means. Nevertheless, a leakage part of CSF cannot be specified by the above-described means in many cases. According to certain statistics, the rate of specifying a leakage part of CSF by the above-described means is only 10 to 20%. In addition, the above-described means have problems of a side effect by a contrast medium and radiation exposure by RI.

PRIOR ART DOCUMENT

Non-Patent Document

Non-patent Document 1: Angelo Franzini et al., Acta Neurochir, 152, pp. 1997-1999 (2010)
Non-patent Document 2: Ansaar Rai et al., AJNR Am J Neuroradial, 26, pp. 2663-2666 (2005)
Non-patent Document 3: Bobby Mehta, Jordan Tarshis, Can JAnesth, 56, pp. 609-613 (2009)
Non-patent Document 4: Keisuke Watanabe et al., J Neurosurg, 114, pp. 1731-1735 (2011)
Non-patent Document 5: Damita L. Thomas et al., Clinical Nuclear Medicine, 34(7), pp. 410-416 (2009)

DISCLOSURE OF THE INVENTION

Problems to be Solved by the Invention

As described above, MRI, CT myelography and RI cerebral scintigraphy have been generally used for diagnosing cerebrospinal fluid hypovolemia, for determining whether CSF leaks or not and for specifying the leakage part. However, the leakage part cannot be often specified in many cases by such means. In addition, the means have problems of a side effect of a contrast medium and radiation exposure by RI.

The objective of the present invention to provide a method for accurately and safely specifying a leakage part of cerebrospinal fluid in a cerebrospinal fluid hypovolemia patient, and a method for effectively treating cerebrospinal fluid hypovolemia with utilizing the specifying method.

Means for Solving the Problems

The inventor of the present invention made extensive studies to solve the above problems. As a result, the inventor completed the present invention by finding that it is possible by injecting a relatively large amount of saline into a bone-marrow space of a spine to determine whether CSF leaks or not and to specify the leakage part in safety and with high accuracy.

Hereinafter, the present invention is described.

[1] A method for specifying a leakage part of cerebrospinal fluid in a cerebrospinal fluid hypovolemia patient, comprising the steps of:

injecting saline into a bone-marrow space of a spine of the cerebrospinal fluid hypovolemia patient, and detecting the cerebrospinal fluid or the injected saline leaked from a dura mater of the spine to specify the leakage part of the cerebrospinal fluid.

[2] The method according to the above [1], wherein an amount of the saline to be injected is 15 mL or more and 30 mL or less.

[3] The method according to the above [1], wherein the cerebrospinal fluid or the injected saline leaked from the dura mater of the spine is detected by a fat-suppressed T2-weighted sagittal image.

[4] The method according to the above [2], wherein the cerebrospinal fluid or the injected saline leaked from the dura mater of the spine is detected by a fat-suppressed T2-weighted sagittal image.

[5] A method for treating cerebrospinal fluid hypovolemia, comprising the steps of:
specifying the leakage part of the cerebrospinal fluid in the cerebrospinal fluid hypovolemia patient by the method according to the above [1], and
covering the specified leakage part by injecting autologous blood to the specified leakage part.

[6] The method according to the above [5], wherein an amount of the saline to be injected is 15 mL or more and 30 mL or less.

[7] The method according to the above [5], wherein the cerebrospinal fluid or the injected saline leaked from the dura mater of the spine is detected by a fat-suppressed T2-weighted sagittal image.

[8] The method according to the above [6], wherein the cerebrospinal fluid or the injected saline leaked from the dura mater of the spine is detected by a fat-suppressed T2-weighted sagittal image.

Effect of the Invention

The present invention method is very safe, since saline is used but a contrast medium and RI are not used. In addition, according to the present invention, it is possible to determine whether CSF leaks or not and to specify the leakage part in an accurate way without difficulty by using a relatively large amount of saline. As a result, it can become possible to reduce the frequency of examination and treatment becomes more effective. The present invention method is therefore very useful for diagnosing and treating cerebrospinal fluid hypovolemia.

MODE FOR CARRYING OUT THE INVENTION

Hereinafter, each step of the present invention method is described. Cerebrospinal fluid is abbreviated to "CSF" and cerebrospinal fluid hypovolemia is abbreviated to "CSFH" below.

1. Step of Preliminarily Shooting Spine

In the present invention, saline is injected into a bone-marrow space of a spine of a CSFH patient. Before the injection of saline, an image of a spine is obtained for comparison with an image after saline is injected.

In the present invention, the term "a CSFH patient" includes not only a patient who is determinately diagnosed with CSFH but also a patient who is suspected of having CSFH. In other words, the term includes a patient who develops symptoms of CSFH, such as headache, but is still not determinately diagnosed with CSFH.

In the present invention, the term "a spine" does not mean an individual vertebra but includes all of vertebrae and means so-called spinal column. For example, saline is injected into a bone-marrow space of a spine mainly by lumbar puncture in the present invention as described later and a dura mater crack which is a cause of CSFH may be inside of the vertebrae into which saline is injected in some cases; however, the dura mater crack is rather inside of another vertebrae in many cases. The term "CSF" means a patient's CSF, and (1) CSF which exists in a bone-marrow space of a patient's spine, (2) CSF leaked in CSFH and (3) CSF leaked due to the injection of saline in the present invention are not particularly distinguished from each other.

A means for shooting a spine is not particularly restricted as long as an image of an aqueous solution such as CSF can be taken in addition to a spine. For example, MRI can be used. In MRI, it is not needed to use a contrast medium or the like. In particular, it is preferred to obtain fat-suppressed T2-weighted sagittal image or short TI inversion recovery image, since a clear image of an aqueous solution and a tissue containing much water can be taken in comparison with an adipose tissue by the means.

2. Step of Injecting Saline

In the present step, saline is injected into a bone-marrow space, particularly subarachnoid space, of a spine of a CSFH patient. As the means for the injection, general lumbar puncture may be employed.

In the present invention, the term "saline" means a sodium chloride aqueous solution which is isotonic or nearly isotonic with a body fluid. For example, 0.9 w/v % sodium chloride aqueous solution can be used as saline. Saline may contain a component other than sodium chloride as long as the saline is isotonic or nearly isotonic with a body fluid. Such a component other than sodium chloride is exemplified by a sugar such as glucose; a potassium salt; a salt of group 2 element, such as a calcium salt and a magnesium salt; an inorganic acid salt such as a chloride salt, a hydrogencarbonate salt and a dihydrogen phosphate salt; and an organic acid salt such as an acetate salt and a lactate salt. In addition, commercially available artificial cerebrospinal fluid and Ringer's solution may be used as saline.

An amount of saline to be injected may be appropriately adjusted. When saline is injected in a larger amount, it may become easier to determine whether CSF leaks or not and to specify a leakage part of CSF. In addition, CSFH is caused by the decrease of amount and pressure of CSF; therefore, even when saline is injected in a large amount, harmful is less and a patient may experience relief of symptoms in some cases. However, when the injected amount is excessively large, a harmful effect may be possibly exerted due to an excessive increase of CSF pressure and leaked CSF amount. For example, an amount of saline to be injected may be adjusted to 15 mL or more and 30 mL or less.

Saline may be injected at a time or in two or more installments. For example, saline may be injected in two or more installments in order not to excessively increase CSF pressure while CSF pressure is measured.

3. Step of Specifying Leakage Part

In the present step, CSF or the injected saline leaked from the dura mater of the spine is detected to specify a leakage part of CSF after saline is injected in the previous step. In the present invention, the phrase "to specify the leakage part of CSF" includes not only literally "to specify the leakage part of CSF" but also "to determine whether CSF leaks or not".

Specifically, an image of the spine is taken in a similar condition to the above-described Step 1 of preliminarily shooting spine, and the obtained image is compared with the image obtained in the above-described Step 1 of preliminarily shooting spine. If CSFH is caused by a crack of a dura mater which covers a spine, at least one of CSF and the injected saline leaks out from the crack due to the injection of saline. Since the leaked amount is relatively large depending on the amount of the injected saline, it is easy to specify the leakage part. If it cannot be observed that CSF or the injected saline leaks out even though saline is injected, it can be judged that CSFH is not caused by the leakage of CSF.

A spine is shot after a time during which at least one of CSF and the injected saline is considered to be leaked when there is a crack in a dura mater of a spine passes from the injection of saline. For example, a spine is shot within 6 hours from immediately after the injection of saline.

4. Step of Epidural Blood Patch

In the present step, after a leakage part of CSF is specified in the above-described Step 3 of specifying leakage part, epidural blood patch is carried out at the leakage part to caulk the leakage part. Epidural blood patch is a method to caulk a leakage part of CSF by injecting autologous blood into extradural space at the leakage part and coagulating the injected blood. According to the present invention, a treatment by epidural blood patch is more effective, since a leakage part of CSF can be accurately specified by the present invention method.

Epidural blood patch may be carried out in an ordinary condition. Specifically, about 30 mL of blood in males and about 20 mL of blood in females is collected from a patient's vein, and the collected blood is injected between the dura mater at the specified leakage part of CSF and the outside adipose tissue. Epidural blood patch may be carried out from one time to three times or so while a patient's condition is monitored.

EXAMPLES

Hereinafter, the present invention is described in more detail with Examples. However, the present invention is not restricted to the following Examples in any way, and it is possible to work the present invention according to the Examples with an additional appropriate change within the range of the above descriptions and the following descriptions. Such a changed embodiment is also included in the technical scope of the present invention.

The abbreviated expressions used in the present invention are described as follows.
  CSF: cerebrospinal fluid
  CSFH: cerebrospinal fluid hypovolemia
  CTM: computed tomographic myelography
  RIC: radioisotope cisternography
  FST2WSI: fat-suppressed T2-weighted image
  EBP: epidural blood patch Example 1

Figure 1:
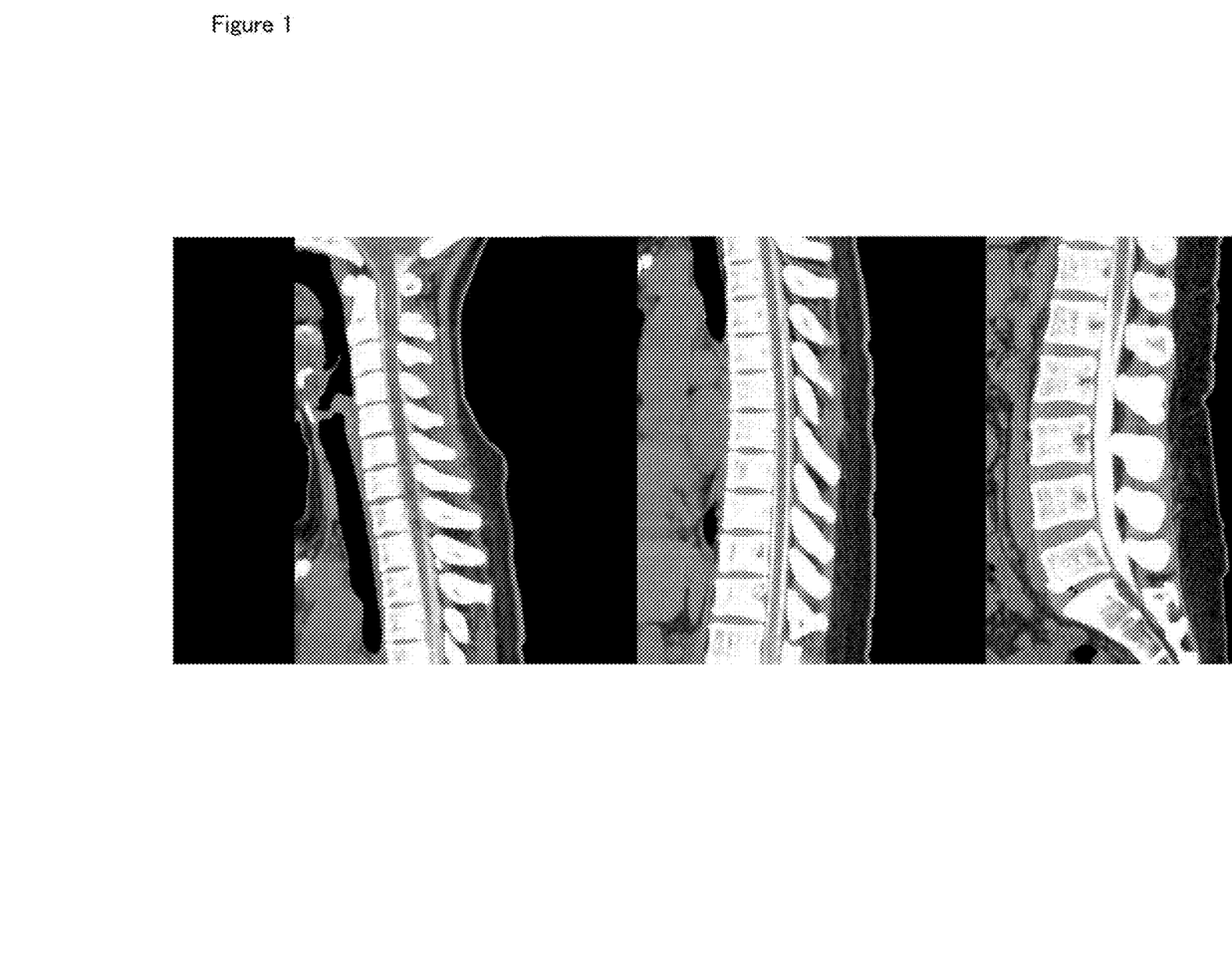
FIG. 1 are computed tomographic myelography images of the spine of a cerebrospinal fluid hypovolemia patient.
Figure 2:
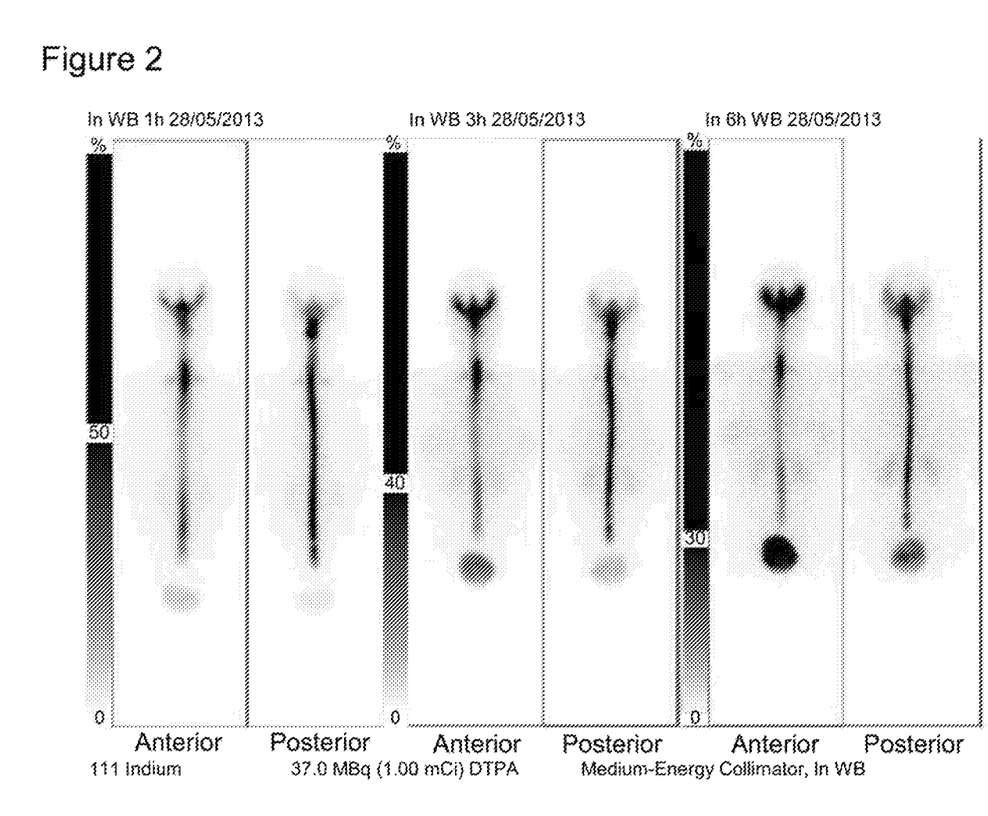
FIG. 2 are radioisotope cisternography images of the spine of a cerebrospinal fluid hypovolemia patient.
Figure 3:
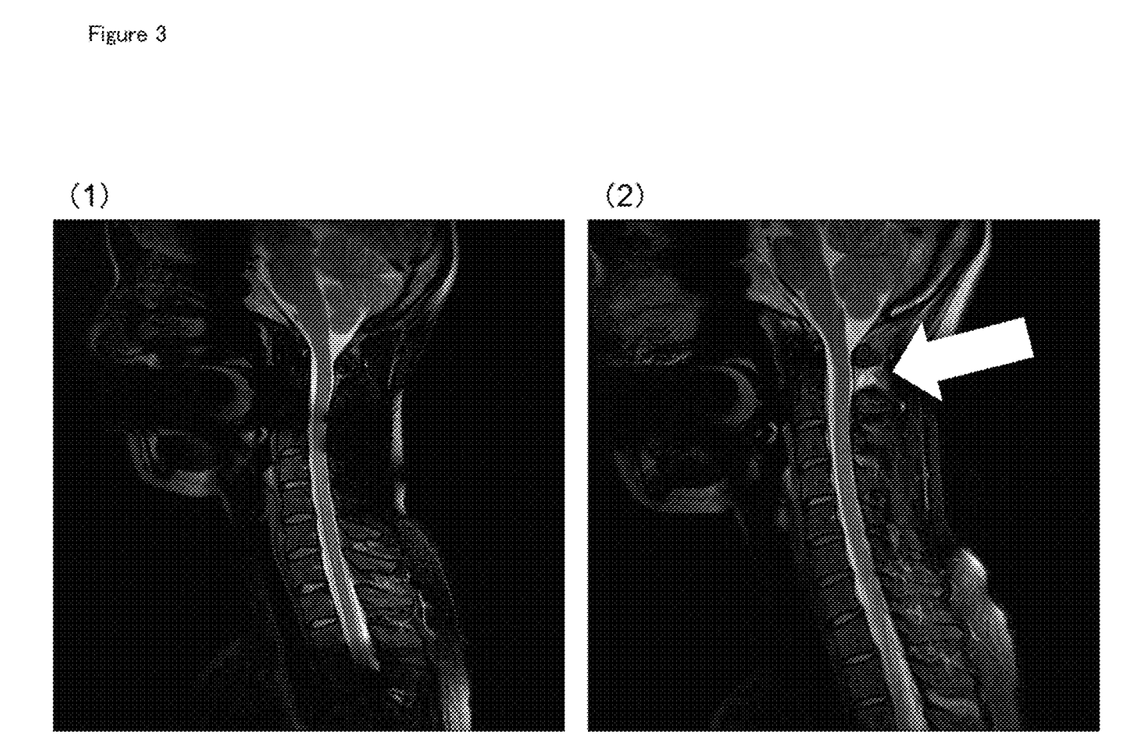
FIG. 3 are fat-suppressed T2-weighted images of the spine of a cerebrospinal fluid hypovolemia patient before and after saline injection.

A 38-year-old woman got a blow on her head while skiing, and then had headache and neck pain. She took an analgesic and an antimigraine drug, but the drugs did not work at all. She was referred to the inventor's hospital on the suspicion of CSFH with a 3-month history of progressively worsening headache and neck pain. Her CSF pressure was not measurable at presentation. Her CTM image is shown as FIG. 1 and RIC image is shown as FIG. 2; however, the leakage part could not be specified by the CTM image and RIC image.

First, a FST2WSI was obtained. Then, 10 mL of saline was injected by lumbar puncture into her subarachnoid space, and then CSF pressure was measured to confirm that there was no excessive rise in CSF pressure. After confirming that the CSF pressure was within normal limits, another 10 mL of saline was further injected. A FST2WSI was obtained again after 3 to 6 hours from the saline injection. The FST2WSI before the saline injection is shown as FIG. 3(1) and the FST2WSI after the saline injection is shown as FIG. 3(2). After the saline injection, leakage was clearly observed between C-1 and C-2 in the neck.

With the patient in a lateral position, a 22-G needle was inserted in the epidural space at the target level under fluoroscopic guidance using the air loss-of-resistance technique, and 18 mL of autologous blood obtained from the patient's right brachial vein was injected. The patient reported complete symptomatic relief without any recurrence at follow-up of 2 months.

Example 2

Figure 4:
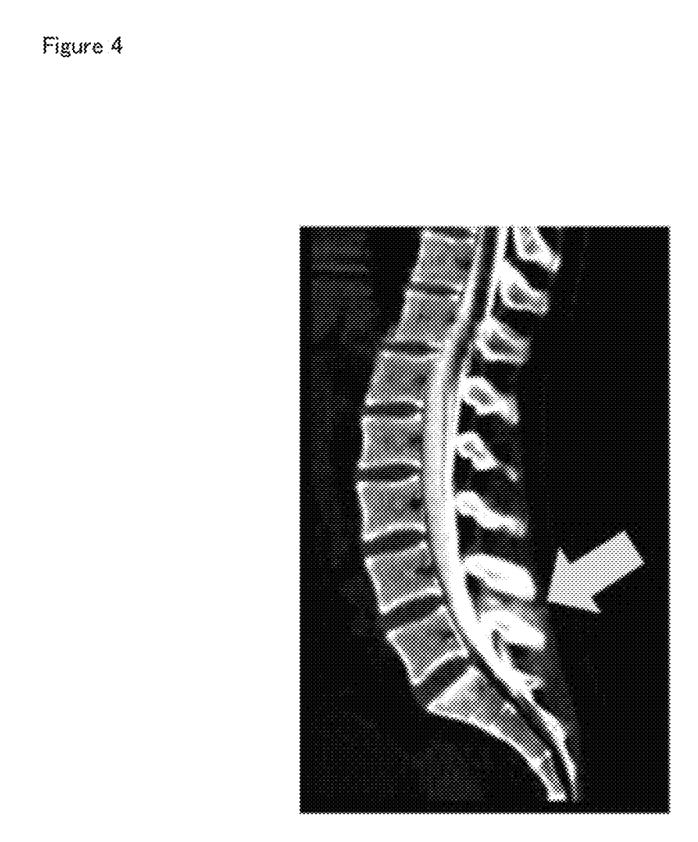
FIG. 4 is a computed tomographic myelography image of the spine of a cerebrospinal fluid hypovolemia patient.
Figure 5:
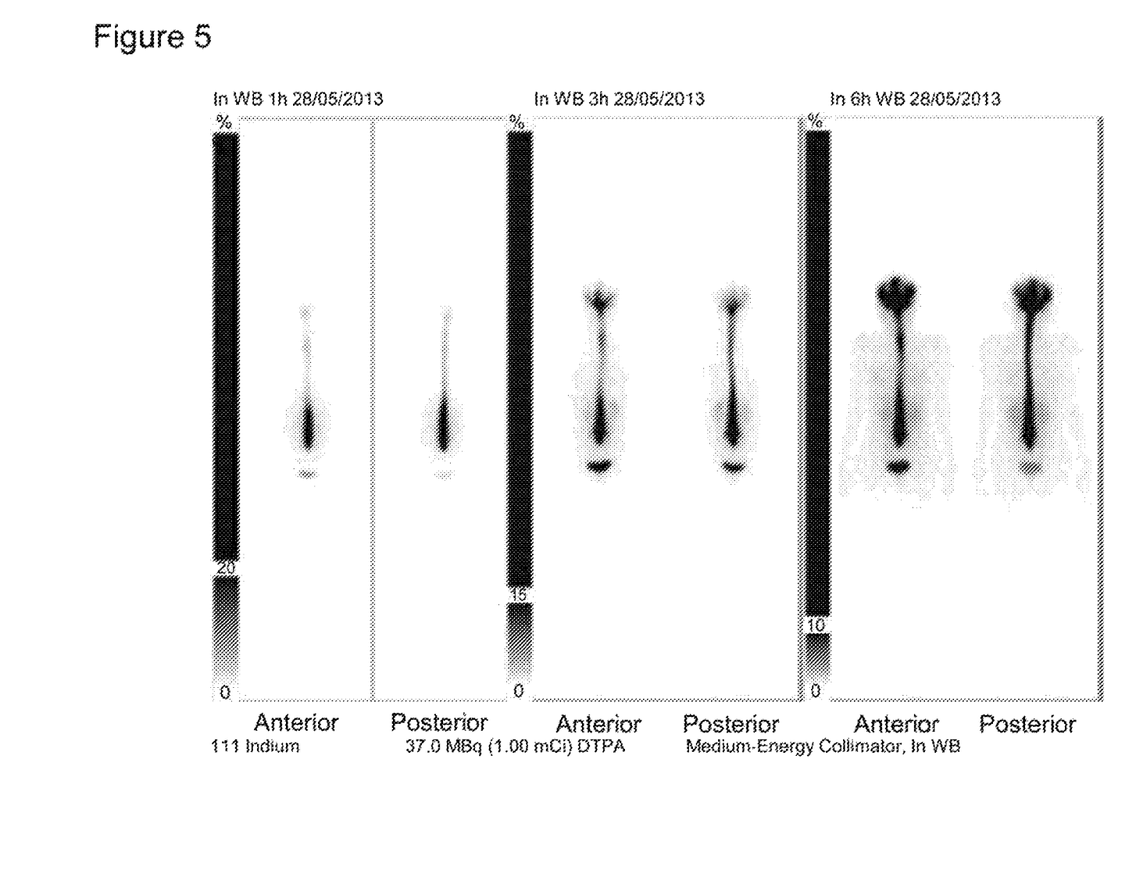
FIG. 5 are radioisotope cisternography images of the spine of a cerebrospinal fluid hypovolemia patient.
Figure 6:
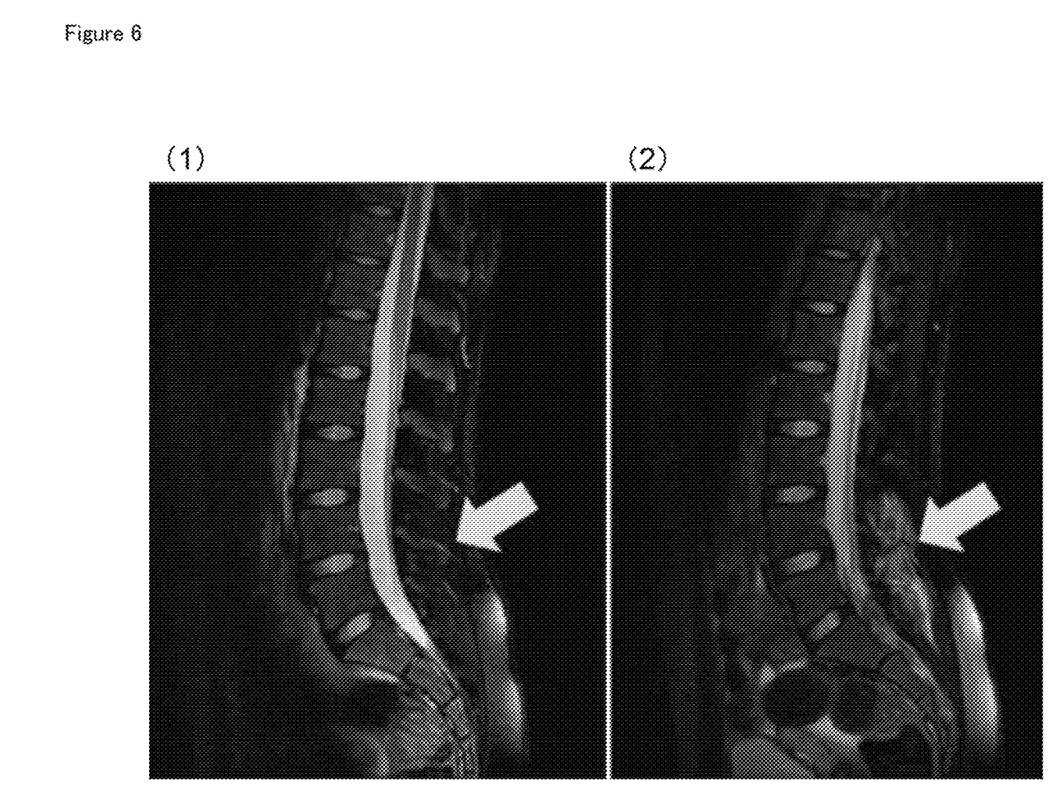
FIG. 6 are fat-suppressed T2-weighted images of the spine of a cerebrospinal fluid hypovolemia patient before and after saline injection.

A 18-year-old woman suffered a traffic accident, and then had headache and neck pain. She was referred to the inventor's hospital on the suspicion of CSFH with a 1-month history of headache and neck pain. Her CSF pressure was 13.5 cm $H_2O$ at presentation, and had decreased to 9 cm $H_2O$ on secondary examination. Her CTM image is shown as FIG. 4 and RIC image is shown as FIG. 5. The leakage part was specified in the lower lumber spine by CTM, but was not specified by RIC.

Similarly to the above Example 1, saline was injected by lumbar puncture into her subarachnoid space and FST2WSIs were obtained before and after the saline injection. The FST2WSI before the saline injection is shown as FIG. 6(1) and the FST2WSI after the saline injection is shown as FIG. 6(2). After the saline injection, leakage was clearly observed in the lower lumber spine.

She was treated by directly injecting 20 mL of autologous blood similarly to the above Example 1, but complained of numbness in both lower limbs. The patient reported complete symptomatic relief without any recurrence, and numbness was improved at follow-up of 5 months.

Example 3

Figure 7:
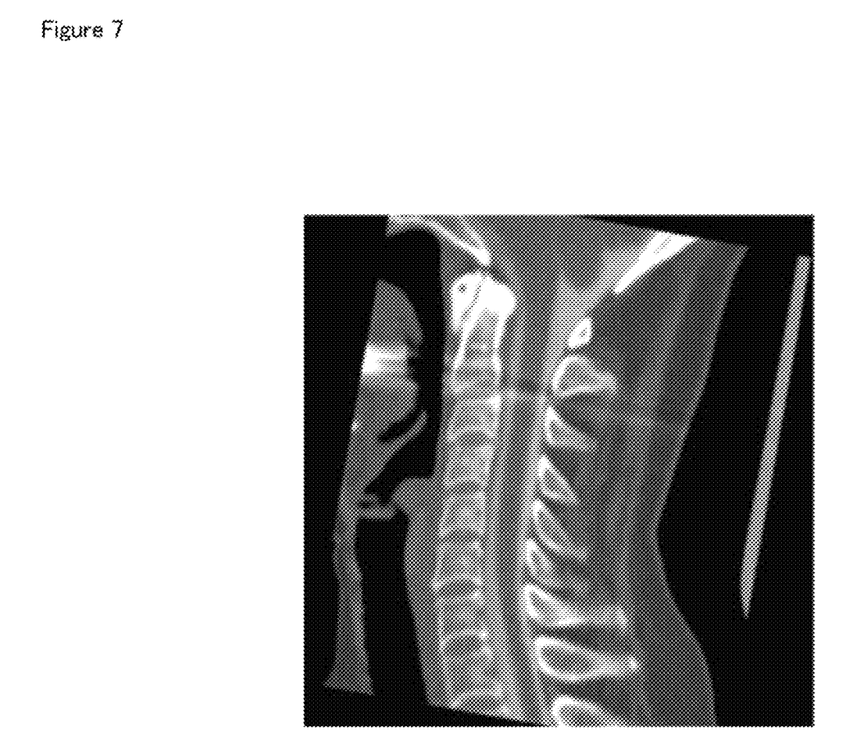
FIG. 7 is a computed tomographic myelography image of the spine of a cerebrospinal fluid hypovolemia patient.
Figure 8:
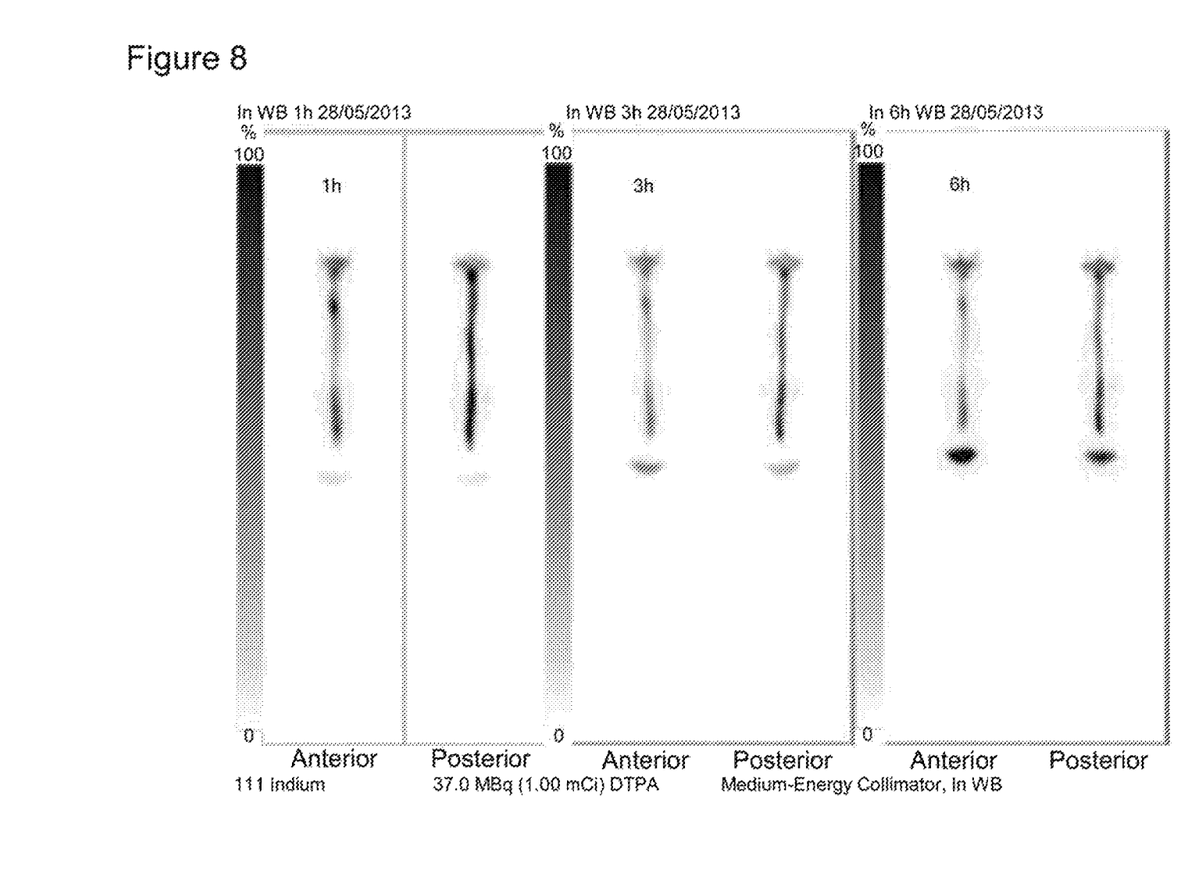
FIG. 8 are radioisotope cisternography images of the spine of a cerebrospinal fluid hypovolemia patient.
Figure 9:
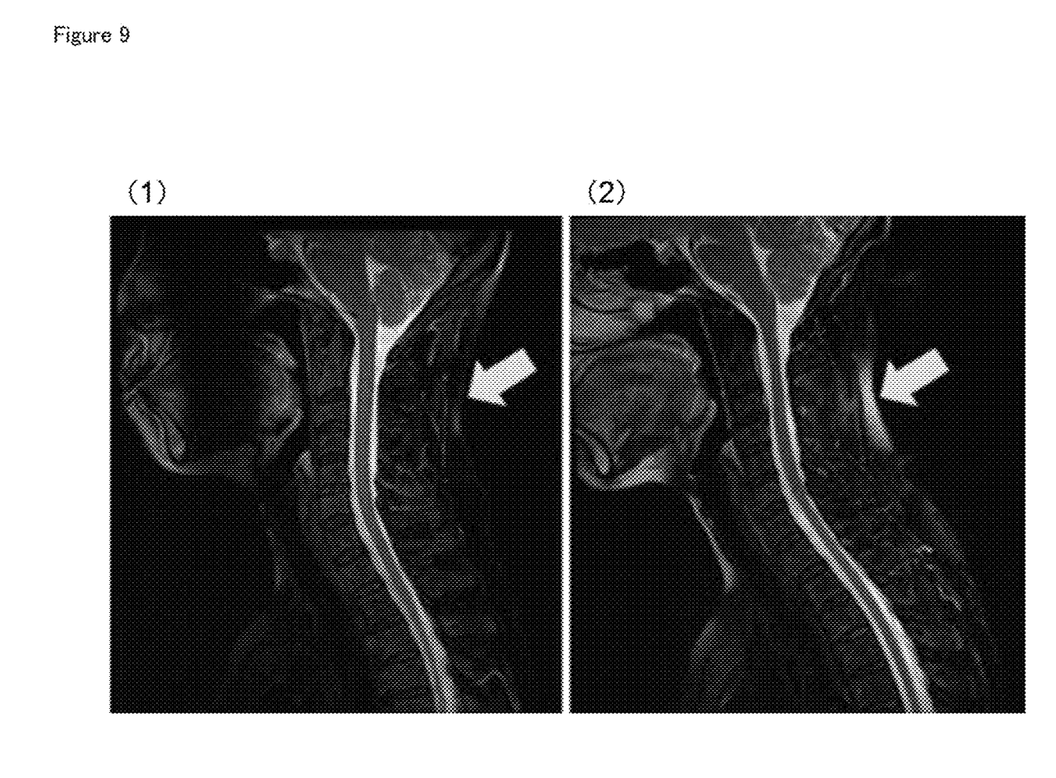
FIG. 9 are fat-suppressed T2-weighted images of the spine of a cerebrospinal fluid hypovolemia patient before and after saline injection.

A 72-year-old woman was referred to the inventor's hospital on the suspicion of CSFH with a 3-month history of progressively worsening headache and neck pain. Her CSF pressure was 2 cm $H_2O$ at presentation. Her CTM image is shown as FIG. 7 and RIC image is shown as FIG. 8. The leakage part was not specified by CTM and RIC.

Similarly to the above Example 1, saline was injected by lumbar puncture into her subarachnoid space and FST2WSIs were obtained before and after the saline injection. The FST2WSI before the saline injection is shown as FIG. 9(1) and the FST2WSI after the saline injection is shown as FIG. 9(2). After the saline injection, leakage was clearly observed in C2-3 in the neck.

Bilateral chronic subdural hematomas (CSDHs) were confirmed on the CT images. Natural healing of subdural hematomas by complete recovery of CSFH had been reported previously; therefore, the inventor prioritized treatment of the CSFH. She was treated by directly injecting 10 mL of autologous blood similarly to the above Example 1, but the patient's state of consciousness deteriorated the next day. The inventor speculated that the improvement of CSFH caused the increased intracranial pressure. The patient's state of consciousness was improved by emergency bur-hole surgery. Thus, the patient reported complete symptomatic relief without any recurrence at follow-up of 3 months.

The invention claimed is:

1. A method for specifying a leakage part of cerebrospinal fluid in a cerebrospinal fluid hypovolemia patient, comprising the steps of:
    injecting saline into a subarachnoid space of a spine of the cerebrospinal fluid hypovolemia patient, wherein the saline does not contain a contrast medium or radio isotope (RI) and
    detecting the cerebrospinal fluid or the injected saline leaked from a dura mater of the spine to specify the leakage part of the cerebrospinal fluid.

2. The method according to claim 1, wherein an amount of the saline to be injected is 15 mL or more and 30 mL or less.

3. The method according to claim 1, wherein the cerebrospinal fluid or the injected saline leaked from the dura mater of the spine is detected by a fat-suppressed T2-weighted sagittal image.

4. The method according to claim 2, wherein the cerebrospinal fluid or the injected saline leaked from the dura mater of the spine is detected by a fat-suppressed T2-weighted sagittal image.

5. A method for treating cerebrospinal fluid hypovolemia, comprising the steps of:
    specifying the leakage part of the cerebrospinal fluid in the cerebrospinal fluid hypovolemia patient by the method according to claim 1, and
    covering the specified leakage part by injecting autologous blood to the specified leakage part.

6. The method according to claim 5, wherein an amount of the saline to be injected is 15 mL or more and 30 mL or less.

7. The method according to claim 5, wherein the cerebrospinal fluid or the injected saline leaked from the dura mater of the spine is detected by a fat-suppressed T2-weighted sagittal image.

8. The method according to claim 6, wherein the cerebrospinal fluid or the injected saline leaked from the dura mater of the spine is detected by a fat-suppressed T2-weighted sagittal image.

* * * * *